United States Patent [19]

Baumgartner

[11] Patent Number: 4,461,280

[45] Date of Patent: Jul. 24, 1984

[54] SURGICAL INSTRUMENT AND PROCESS

[76] Inventor: George C. Baumgartner, P.O. Box 680, 890 Garfield Ave., Libertyville, Ill. 60048

[21] Appl. No.: 488,343

[22] Filed: Apr. 25, 1983

Related U.S. Application Data

[62] Division of Ser. No. 216,374, Dec. 15, 1980, Pat. No. 4,396,021.

[51] Int. Cl.³ .............................................. A61J 1/00
[52] U.S. Cl. ...................................... 128/1.2; 604/51; 604/57; 604/60; 604/93; 604/164; 604/170
[58] Field of Search ..................... 128/1.1, 1.2; 604/49, 604/51, 54, 57, 59–61, 93, 164, 166, 170

[56] References Cited

U.S. PATENT DOCUMENTS

| | | | |
|---|---|---|---|
| 1,920,006 | 7/1933 | Dozier | 604/170 |
| 2,691,370 | 10/1954 | Wallace | 128/6 |
| 3,477,423 | 11/1969 | Griffith | 128/754 |
| 3,595,217 | 7/1971 | Rheinfrank | 128/754 |
| 3,858,577 | 1/1975 | Bass et al. | 128/8 |
| 3,870,036 | 3/1975 | Fiore | 128/6 |
| 3,921,632 | 11/1975 | Bardani | 604/60 |
| 3,929,123 | 12/1975 | Jamshidi | 128/754 |
| 3,995,619 | 12/1976 | Glatzer | 128/749 |
| 4,318,401 | 3/1982 | Zimmerman | 604/51 X |
| 4,402,308 | 9/1983 | Scott | 128/1.2 |

OTHER PUBLICATIONS

Muir, Joseph, "Advantages of the Loading Slot in Radium Emanation Implantation", *Journal of Urology*, vol. XI, No. 3, Mar. 1924, pp. 319–325.

*Primary Examiner*—Kyle L. Howell
*Assistant Examiner*—Christine A. Fukushima

[57] ABSTRACT

A method of providing medical treatment of the prostate area. A urethrally inserted apparatus having an outer sheath, and a removable obturator located within the sheath during insertion of the sheath into the urinary tract by way of the externally urethra orifice in the penis is disclosed. Once the sheath is inserted, the obturator portion is removed and a medication depositing structure is inserted into the sheath. The depositing structure carries selected medication, as for example, radioactive iodine seeds. The obturator may be provided with means for inserting a viewing lens element to assure that the appropriate location adjacent to the prostate is obtained. Once the medication depositing structure is adjacent a selected area in the prostate, the prostate is pierced by the depositing structure so as to position the medication within the selected area. The medication is released and the deposition structure is withdrawn from the sheath. Thereafter, the sheath is withdrawn from the urethra.

1 Claim, 5 Drawing Figures

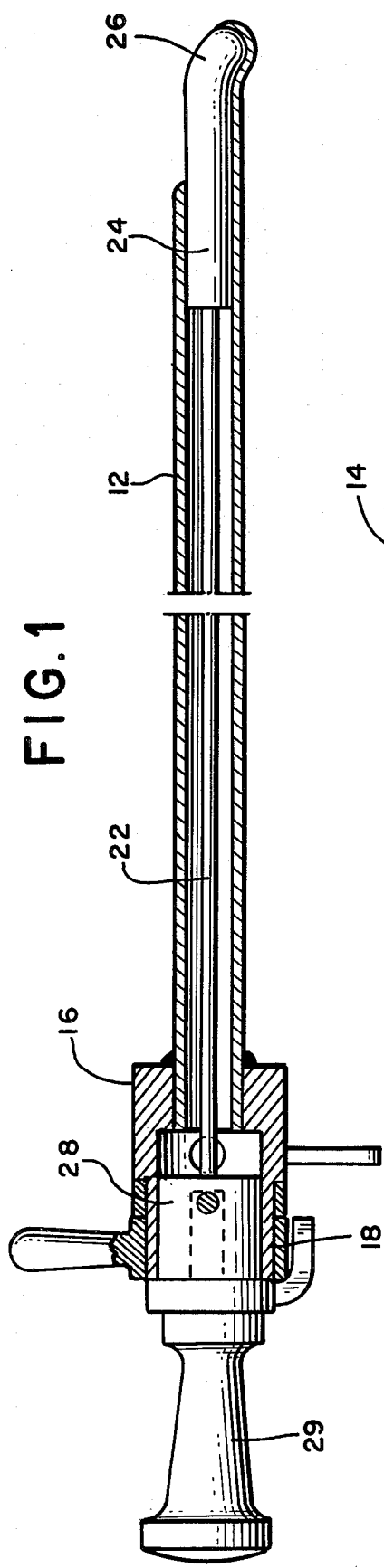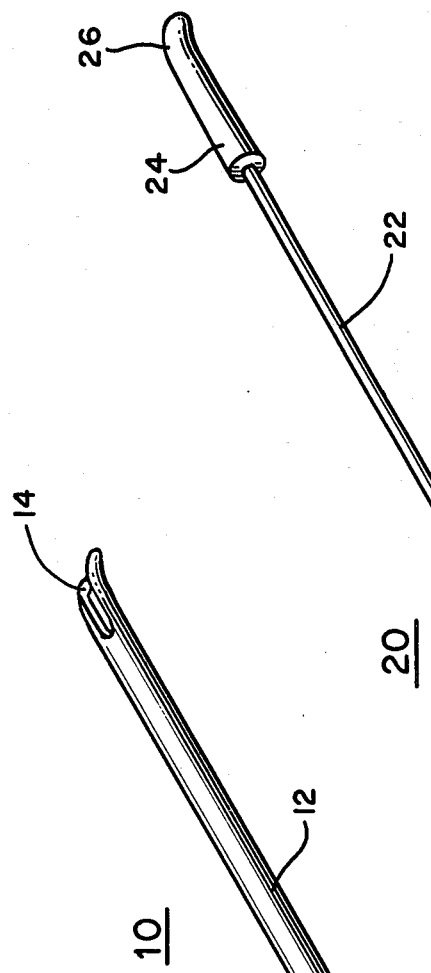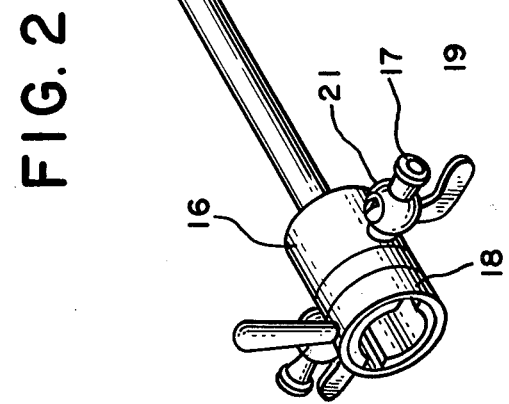

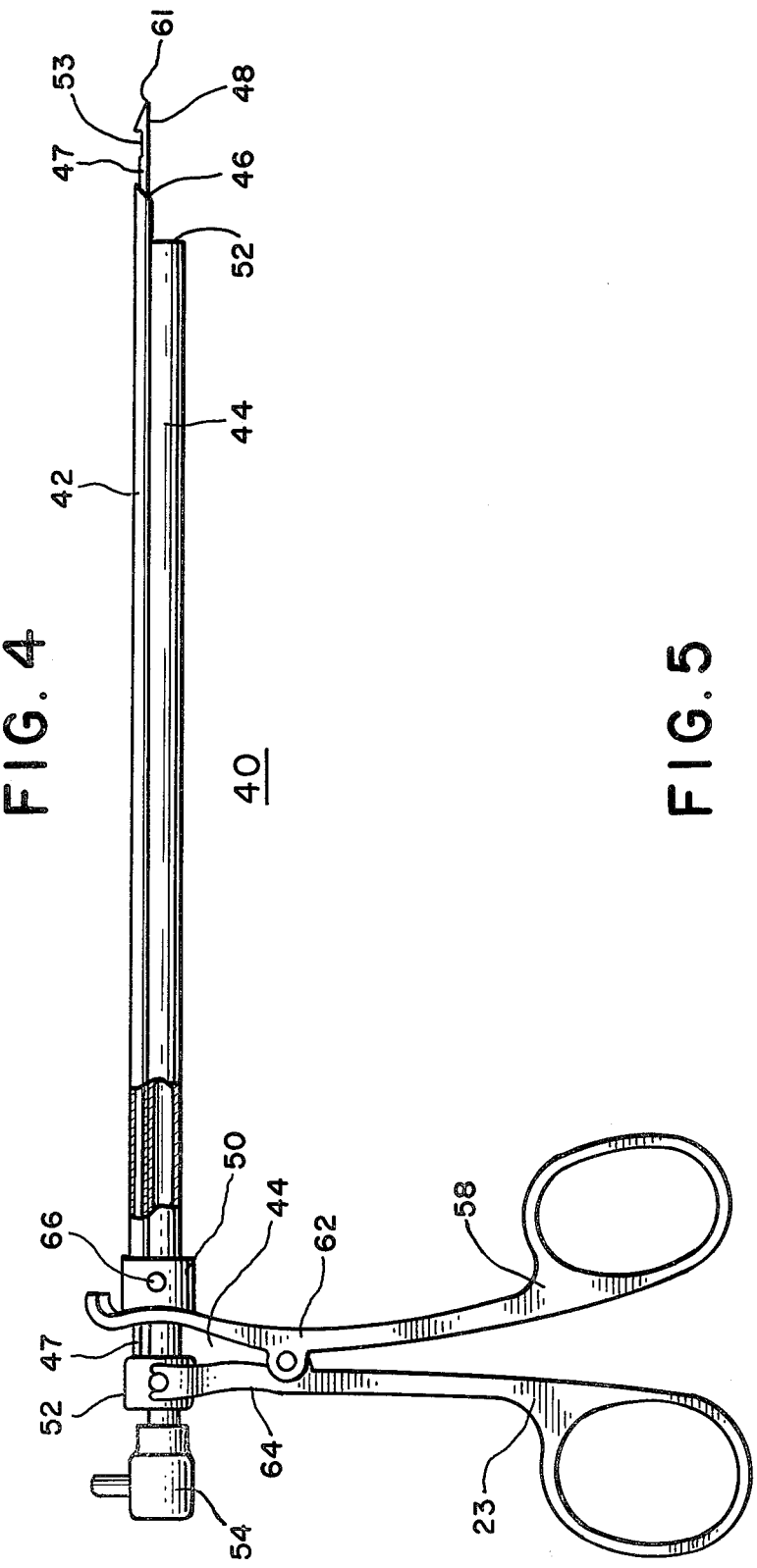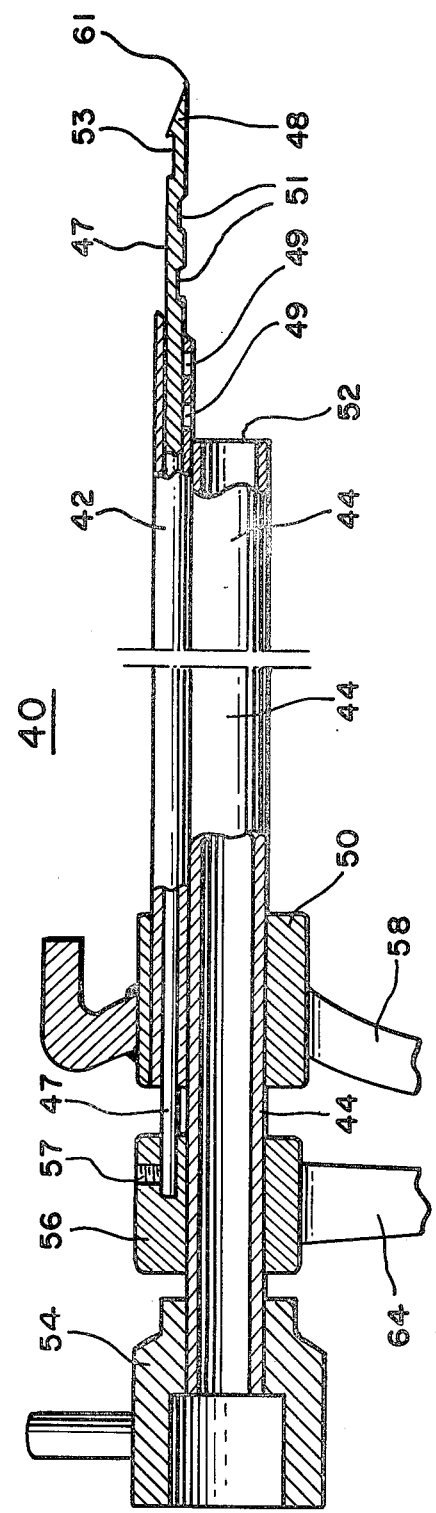

SURGICAL INSTRUMENT AND PROCESS

This application is a division of application Ser. No. 06/216,374, filed Dec. 15, 1980 now U.S. Pat. No. 4,396,021.

BACKGROUND OF THE INVENTION

The present invention relates to surgical instruments and techniques and, more particularly, to an apparatus and method for obtaining a biopsy sample of the prostate through the urinary tract.

In the prior art, there are a variety of apparatus and techniques used to obtain biopsy samples from different tissues for testing. Generally, the devices are designed for specific applications and include special configurations and arrangements for those applications. Due to the location of certain tissues, for example, the prostate, not all devices are capable of use in obtaining the biopsy sample.

In the past, biopsy samples taken from the prostate have been used to aid in the diagnosis and treatment of prostate malignancies. The devices which have been developed generally include a sheath which is inserted into the rectum of a patient and a needle which is then advanced with the sheath to pierce the rectal wall and obtain a sample of the prostate. This particular apparatus enables the sample to be withdrawn and analyzed for a determination of the presence of any malignancy in the tissue.

Other types of biopsy apparatus are known, but their configuration generally prevents their use in the manner described. In addition, the technique of removing the biopsy sample through the rectum produces infection and bleeding in the patient and is not conducive to early cancer diagnosis.

In addition to the above-noted sampling problems, the instruments and techniques of the prior art have been deficient in enabling medical treatment of prostate problems once they have been detected. The most common technique for prostate treatment involves surgically cutting an opening into the prostate area into which medication or other treatment can be introduced. In addition to being more complex and costly, such procedures expose the patient to increased chances of infection and a longer healing period.

There is therefore a need for alternative apparatus and techniques for obtaining biopsy samples of the prostate to diagnose malignancies and other illnesses and to provide for less complicated treatment once a problem has been detected. Thus the present invention has been developed to overcome the specific shortcomings of the above known and similar techniques and, more particularly, to provide an improved technique for obtaining prostate biopsy samples and providing prostate treatment.

SUMMARY OF THE INVENTION

In accordance with the present invention, an elongated hollow sheath is provided having an opening for retaining an obturator element at one end and a coupling element at the opposite end. The device includes a removable obturator portion which is axially inserted into the sheath and retained by the coupling element so that the obturator portion in cooperation with the sheath forms a substantially solid shaft for insertion into the urethra. A second removable sampling portion includes two elongated tubes mounted adjacent and running parallel to one another and coupled to a mounting element at one end thereof. One of the tubes includes a shaft which extends axially therethrough and terminates in a pointed harpoon-type cutting element extending from one end thereof. The harpoon shaft extends through the tube and mounting element and is coupled to a movable member controlled by a scissors lever arrangement extending from the mounting element. By moving the scissors arms, the harpoon shaft slides axially in the associated tube to cause a cutting action at one end thereof.

In operation, the sheath and obturator combination is first inserted into the urethra to the desired position. The obturator portion is then removed and the biopsy sampling portion inserted through the sheath to the sampling area. A lens and light pipe structure can then be inserted through the second tube adjacent to the harpoon shaft to view the sampling area. The sampling portion is then subsequently manipulated to the desired sampling area and the scissors control is used to pierce and sever the desired sample. Added manual control can be achieved by finger manipulation within the rectum of the patient. Thereupon, the sampling portion is removed from the sheath to obtain the biopsy sample. The sheath can be removed from the urethra following removal of the sampling portion.

The sampling portion is also constructed so that medication can be introduced into the prostate area when treatment is necessary. In that instance, rather than taking a biopsy sample, the harpoon shaft and tube in the sampling structure cooperate to retain medication which can be deposited in the prostate by manipulation of the harpoon shaft once the tip has penetrated the prostate.

It is a feature of the invention to provide a technique for treating the prostate with access through the urethra.

It is yet another feature of the invention to provide a modified cystoscope for depositing medication into the prostate area through the urethra.

It is still a further feature of the invention to provide a surgical instrument capable of both extracting biopsy samples and providing prostate treatment through the urethra.

These and other novel features of the invention will become apparent from the following detailed description when taken with the accompanying drawings wherein:

BRIEF DESCRIPTION OF THE DRAWINGS

FIG. 1 is a side view of the modified cystoscope in accordance with the present invention having the inserted obturator portion.

FIG. 2 is a perspective view of the sheath portion of the modified cystoscope with the obturator portion removed.

FIG. 3 is a perspective view of the obturator portion used in connection with the sheath of FIG. 2.

FIG. 4 is a side view showing the sampling portion of the modified cystoscope in accordance with the present invention.

FIG. 5 is a cross-sectional side view of the sampling portion of FIG. 4.

DETAILED DESCRIPTION OF A PREFERRED EMBODIMENT

Turning now to FIG. 1, a modified cystoscope 10 is shown having an obturator portion 20 coupled therein.

The cystoscope 10 generally includes a sheath 12 which may be of any desirable configuration but suitably shaped for easy insertion into the urethra. The sheath 12 has an opening 14 at one end thereof configured to retain the tip 26 of an obturator portion 20. The other end of the sheath 12 is rigidly retained in a mounting member 16 and extends through the mounting member and locking member 18. The mounting member 16 retains a locking member 18 for conventional construction so that the locking member 18 rotates relative to member 16 to align slots for receiving the obturator portion 20. When the obturator portion 20 is inserted into the sheath, projecting pins 30 engage those slots and locking member 18 can be rotated to securely retain the obturator in position in a well-known manner. Inlets 17, located on opposite sides of mounting member 16, also extend through and into the channel extending through the sheath 12 to provide passages to the interior of sheath 12. Valve arms 19 are used to control a valve 21 on each inlet 17 to allow control of a gas or liquid through the passages 17 in a wellknown manner.

The obturator portion 20 shown in FIG. 3 generally has a shaft 22 terminating in a solid portion 24. The portion 24 has a tip 26 configured to provide a smooth terminus to the tip surrounding opening 14 of sheath 12. At the opposite end of the shaft 22 is a retaining block member 28 which is configured to be received by the retaining and locking members 16 and 18 of the cystoscope 10 in FIG. 1. Member 28 includes projecting pins 30 extending from opposite sides of the member 28. The pins 30 engage corresponding slots (not shown) in members 16 and 18 and are retained in a locked position when the rotating member 18 is moved to an appropriate position in accordance with the prior art. A gripping member 29 is usually attached to the member 28 to allow easy insertion and removal of the obturator 20 into the sheath 12.

Referring now to FIG. 4, the sampling portion of the modified cystoscope is generally shown at 40. The sampling portion includes adjacent parallel tubes 42 and 44 which are attached to one another and have a length which allows the tubes to extend through the sheath 12 and project from the opening 14. The tube 42 terminates in a forward end 46 which is tapered to form a blade-type surface. A shaft 47 extends through the tube 42 and terminates in a harpoon-blade structure generally shown at 48. The harpoon-blade structure may be oriented in any manner relative to the taper on the tube 42 so long as the harpoon edge 48 causes a severing action when drawn back into the tube 42 past the edge 46. The harpoon end 48 also includes a tip 61 which is used to puncture the tissue which is to be sampled and a pocket 53 formed behind the harpoon-type barb.

Adjacent the edge 46, a series of small openings 49 are axially aligned and spaced along the surface of tube 42 parallel to the shaft 47 running through the tube 42. Cooperating pockets 51 are located along the length of the shaft 47 so that by manipulation of the shaft axially along the tube 42, the openings 49 will align with the pockets 51 so that access to each of the pockets 51 is provided through the corresponding openings 49. The pockets 51 are shaped to receive medication (i.e. radio-active iodine seeds) through the openings 49, which medication can be retained in the pockets 51 by moving the shaft 47 axially along tube 42 to cause misalignment of the pockets 51 and openings 49 once the medication has been inserted. Release of the medication can be accomplished by realigning the pockets 51 and openings 49 by manipulation of the shaft 47.

The tube 44 terminates in an opening 52 which is adjacent the edge 46 of the tube 42. Tubes 42 and 44 are retained by a support member 50. The tube 42 terminates within the support member 50 while the tube 44 extends through and into an end element 54. The support member 50 includes projecting pins 66 similar to the projecting pins 30 on obturator portion 20. The pins 66 are retained by locking ring 18 when the sampling portion is inserted into the sheath 12. The shaft 47 extends through the tube 42 and support member 50 and is rigidly attached to element 56 located between members 50 and 54. The shaft 47 is slidably retained in the tube and support member 50 and removably secured within member 56 by a fastener (i.e. set screw) 57.

At the rear end of member 50, a scissors arm 58, having a pivotal coupling 62, is coupled generally perpendicular thereto. A second scissors arm 60 is pivotally coupled to 62 and includes a portion 64 rigidly attached to the member 56. As can be seen in FIG. 4 when the scissors arms 58 and 60 are moved relative to each other, the member 56 is caused to slidably move along tube 44 causing shaft 47 and thus harpoon tip 48 to reciprocate in tube 42. The positioning of the harpoon tip 48 relative to the end 46 is such that upon movement of member 56, the harpoon structure moves forward of end 46 and can be withdrawn into the opening formed by member 46. The tube 44 extends through the element 54 and provides an opening in the rear thereof for insertion of a light tube and viewing lens.

The elements of cystoscope 10, obturator 20 and sampling portion 40 are generally formed from metals usually employed in surgical instruments. It is anticipated, however, that any materials suitable for the uses intended may be used without detracting from the teachings of the present invention. Likewise, the locking mechanism 18, while wellknown in the art, may be modified to accommodate various structures consistent with the present invention.

In accordance with the present invention, the modified cystoscope shown in FIGS. 1 through 5 may be used to obtain a biopsy sample of the prostate through the urethra. In the prior art, the normal procedure for obtaining the prostate sample was to provide rectal or skin insertion of a sampling device to puncture the prostate through the rectal wall or perineal skin. As has been previously noted, the process and the apparatus used to accomplish the sampling has generally been uncomfortable and relatively dangerous and therefore objectionable for patient treatment. By use of the present invention, the prostate sampling can be made through the urethra, thereby eliminating the disadvantages of the prior art techniques and apparatus.

In operation, the obturator 20 is first inserted into the sheath 12 so that the tip portion 26 extends through the opening 14 in sheath 12. The tip portion 26 is generally formed to have rounded smooth edges cooperating with rounded smooth edges on the sheath at opening 14. When positioned and locked by member 18, the obturator portion 20 and sheath portion 12 form a generally rigid unitary rod for insertion into the urethra through the external urethral orifice in the penis of the patient. Accordingly, the sheath and obturator portion are moved together through the urethra until the desired position of the opening 14 is located. At that time, the locking ring 18 is rotated and the obturator portion 20 removed to provide a canal through sheath 12 from the exterior of the urethra to the opening 14 adjacent the prostate.

At this time, the sampling portion 40 is inserted through the sheath 12 until the tubes 42 and 44 have their openings positioned at the desired area. Prior to sampling, the tube 44 can accommodate a lens and light pipe structure which may be inserted to extend through opening 52 for viewing the area to be sampled. Any lens or viewing structure is inserted through the rear end of tube 44 retained in end member 54 exterior to the sheath 12. Using the viewing or lens structure extending through opening 52, the positioning of the end 46 of tube 42 can be located relative to the area to be sampled with the surgeon's finger in the rectum on the patient's prostate. Once this has been done, with the surgeon's other hand, the member 50 can be locked in retaining ring 18 relative to the sheath 12 or it can be independently positioned without the locking arrangement. At that time, the scissors arms 58 and 60 can be manipulated to cause the point 61 of harpoon tip 48 to puncture the prostate area to be sampled under the surgeon's tactile control. The lower hook of the harpoon tip will retain a portion of the tissue punctured and upon withdrawal and movement of the shaft 47, will engage the tip 46 to cause a severing action of the tissue. As the shaft 47 is further withdrawn by movement of element 56 rearwardly, the tissue sample will be retained in the pocket 53 of harpoon 48 within the tube 42. Thereafter, the sampling portion 40 may be withdrawn by movement rearwardly in the sheath 12 to remove the sampling structure from the sampling area. After the sampling structure 40 has been removed, the sheath 12 may also be removed from the urethra, completing the process.

Once diagnosis of the problem has been achieved and treatment is required, the instrument can be used to provide treatment to the prostate area. In this instance, the sheath 12 retaining obturator 20 is again inserted into the urethra through the urethral orifice of the penis until the opening 14 is adjacent the prostate area to be treated. The obturator 20 is then withdrawn and the sampling portion 40 inserted into the sheath 12. In this instance, however, prior to insertion of the sampling portion 40, medication, such as radioactive iodine seeds, are first inserted into the pockets 51 in shaft 47 through the aligned openings 49. Once the seeds are in place, the shaft 47 is moved axially to misalign the pockets 51 and openings 49 and retain the seeds in the pockets 51 surrounded by the interior wall of tube 42.

To provide treatment, the sampling portion 40 is then inserted through the sheath 12 so that the harpoon tip penetrates the prostate area. After penetration, the harpoon tip and end 46 of tube 42 will be in the prostate area. Thereafter, by manipulation of the shaft 47, the pockets 51 can be realigned with openings 49 so that the iodine seeds can be expelled into the prostate area. Once the seeds have been expelled, the sampling portion 40 can be removed and reused to insert other seeds in different areas prior to removal of the sampling portion 40 and sheath 12 upon completion of treatment.

As an alternative to the above treatment structure, the sampling portion 40 may be constructed without the pockets 51 and openings 49. In this instance, an iodine seed could be deposited in the pocket 53 and retained by withdrawing the harpoon tip into the tube 42 prior to insertion of the portion 40 into the sheath 12. Thereafter, the portion 40 could be inserted to penetrate the prostate as described above, and the shaft 47 moved forward to open the pocket 53 into the prostate and release the iodine seed.

As can be seen by the above description, the present invention provides a novel apparatus and technique for obtaining prostate biopsy samples and for providing prostate treatment. The present invention allows the insertion of a sampling device into the urethra with minimal discomfort to the patient. By use of the obturator structure 20 in the sheath 12, the forward end of the cystoscope is formed so that easy insertion is facilitated. Thereafter, the obturator can be removed and the sampling portion 40 of the modified cystoscope inserted. The sampling portion 40 provides for easy puncture and removal of a biopsy sample along with a cooperating shaft for lens positioning and inspection of the sample area. The insertion of the sampling portion 40 allows and facilitates the ready acquisition of a biopsy sample without rectal penetration. The use of the sampling portion 40 with the sheath 12 also allows treatment of the prostate through the urethra with a simple technique not requiring additional surgical instruments. All of the above are features which are not shown by any of the prior art.

Although the invention has been described with particular reference to specific structural configurations, it is obvious that many modifications can be made without departing from the present invention. By way of example, the sample could be taken through the sheath by a sampling portion of another construction, or by any known type of sampling tool compatible with the structural cooperation disclosed. A variety of such structures used for other purposes in the prior art could be employed with the present structure to practice the inventive technique.

Likewise, in lieu of providing pockets in the harpoon structure used for sampling, a separate shaft having such pockets could be formed and interchanged with shaft 47 merely by releasing and replacing shaft 47 in member 56 upon loosening of set screw 57.

Obviously, many other modifications and variations of the present invention are possible in light of the above teachings. It is therefore to be understood that within the scope of the appended claims, the invention may be practiced otherwise than as is specifically described.

I claim:

1. A medical process for treating the prostate area by selectively depositing medication to the prostate area, comprising:

selecting an elongated sheath shaped for insertion into the urethra, said sheath having an opening at one end thereof;

inserting an obturator having a shaft with a solid end portion into the sheath so that the solid end portion is retained within said opening;

inserting the obturator and sheath into the urethra through the external urethra orifice in the penis;

moving the obturator and sheath through the urethra so that the solid end portion is positioned to a location adjacent a selected area in the prostate;

removing the obturator portion from the sheath once said selected area is obtained;

selecting a medication depositing structure retaining medication wherein said structure has two adjacent parallel tubes, one of which provides a channel for receiving a viewing lens structure and the other of which includes at least one opening along the tube and a reciprocating shaft having at least one medication receiving pocket capable of being aligned with said opening upon movement of said shaft, for depositing prostate medication;

inserting said medication deposition structure into and through the sheath to said location adjacent a selected area;

viewing the location adjacent a selected area in the prostate through said viewing lens in the medication depositing structure;

piercing the prostate with said depositing structure to position the medication at said selected area;

releasing the medication from the depositing structure into the prostate at said selected area;

withdrawing the depositing structure from the sheath; and withdrawing the sheath from the urethra.

* * * * *